United States Patent
Robert et al.

(10) Patent No.: US 12,394,138 B2
(45) Date of Patent: Aug. 19, 2025

(54) RENDERING OF B-MODE IMAGES BASED ON TISSUE DIFFERENTIATION

(71) Applicant: KONINKLIJKE PHILIPS N.V., Eindhoven (NL)

(72) Inventors: Jean-Luc Francois-Marie Robert, Cambridge, MA (US); Francois Guy Gerard Marie Vignon, Andover, MA (US); Benoit Jean-Dominique Bertrand Maurice Mory, Medford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 170 days.

(21) Appl. No.: 18/028,945

(22) PCT Filed: Sep. 26, 2021

(86) PCT No.: PCT/EP2021/076422
§ 371 (c)(1),
(2) Date: Mar. 28, 2023

(87) PCT Pub. No.: WO2022/069377
PCT Pub. Date: Apr. 7, 2022

(65) Prior Publication Data
US 2023/0377246 A1    Nov. 23, 2023

Related U.S. Application Data

(60) Provisional application No. 63/084,870, filed on Sep. 29, 2020.

(51) Int. Cl.
*G06T 15/08* (2011.01)
*G06T 7/00* (2017.01)
(Continued)

(52) U.S. Cl.
CPC ............ *G06T 15/08* (2013.01); *G06T 7/0014* (2013.01); *G06T 7/11* (2017.01); *G06T 7/40* (2013.01);
(Continued)

(58) Field of Classification Search
CPC ..... A61B 8/5246; A61B 8/5269; G06T 19/20; G06T 15/08; G06T 7/11; G06T 7/0014;
(Continued)

(56) References Cited

U.S. PATENT DOCUMENTS 6,443,896 B1    9/2002  Detmer
6,530,885 B1    3/2003  Entrekin et al.
(Continued)

FOREIGN PATENT DOCUMENTS

| CA | 2420607 C * | 1/2012 | ............ A61B 34/35 |
| WO | 2018127497 A1 | 8/2019 | |
| WO | 2022038208 A1 | 2/2022 | |

OTHER PUBLICATIONS

Sassaroli E, Crake C, Scorza A, Kim DS, Park MA. Image quality evaluation of ultrasound imaging systems: advanced B-modes. Journal of applied clinical medical physics. Mar. 2019;20(3):115-24.*

(Continued)

*Primary Examiner* — Phu K Nguyen (57) ABSTRACT

In some examples, tissue types in B-mode images may be differentiated by multiparameter imaging and/or other segmentation techniques. The tissue types may be used to assign material properties to voxels of the B-mode image, such as color, translucency, and reflectivity. The material properties may be used to generate a rendered image. In some examples, one or more of the material properties assigned to the voxels may correspond to values of tissue parameters acquired during multiparameter imaging. The
(Continued)

rendered image may include data based on both the B-mode image and the multiparameter imaging.

18 Claims, 8 Drawing Sheets

(51) Int. Cl.
    *G06T 7/11*         (2017.01)
    *G06T 7/40*         (2017.01)
    *G06T 15/50*       (2011.01)

(52) U.S. Cl.
    CPC .... *G06T 15/50* (2013.01); *G06T 2207/10132* (2013.01); *G06T 2207/20084* (2013.01); *G06T 2207/30004* (2013.01); *G06T 2210/41* (2013.01)

(58) Field of Classification Search
    CPC ......... G06T 15/50; G06T 7/0012; G06T 7/40; G06T 2207/20084; G06T 2210/41; G06T 2219/2012; G06T 2207/30004; G06T 2207/10132
    USPC ........................................................ 345/418
    See application file for complete search history.

(56) References Cited

U.S. PATENT DOCUMENTS

| | | | |
|---|---|---|---|
| 7,957,572 | B2 | 6/2011 | Von Berg et al. |
| 10,755,810 | B2* | 8/2020 | Buckler ................ G16H 30/40 |
| 11,701,086 | B1* | 7/2023 | Singh ...................... A61B 8/58 |
| | | | 600/442 |
| 2019/0147645 | A1 | 5/2019 | Mory et al. |
| 2019/0251755 | A1 | 8/2019 | Douglas et al. |
| 2019/0318534 | A1 | 10/2019 | Mory et al. |
| 2020/0405264 | A1* | 12/2020 | Labyed ............... G01S 7/52073 |
| 2021/0015456 | A1* | 1/2021 | Chiang ................ A61B 8/0883 |
| 2022/0245793 | A1* | 8/2022 | Gilbert ................. G06T 7/0012 |
| 2023/0117281 | A1* | 4/2023 | Peng ..................... A61B 8/488 |
| | | | 345/591 |
| 2023/0240662 | A1* | 8/2023 | McLaughlin ........ A61B 8/0825 |
| | | | 600/437 |
| 2024/0324988 | A1* | 10/2024 | Johnson ............... A61B 8/4483 |

OTHER PUBLICATIONS

Perperidis A. Postprocessing approaches for the improvement of cardiac ultrasound b-mode images: A review. IEEE transactions on ultrasonics, ferroelectrics, and frequency control. Feb. 8, 2016;63(3):470-85.*

Agrawal S, Dangi A, Frings N, Albahrani H, Ghouth SB, Kothapalli SR. Optimal design of combined ultrasound and multispectral photoacoustic deep tissue imaging devices using hybrid simulation platform. InPhotons Plus Ultrasound: Imaging and Sensing 2019 Feb. 27, 2019 (vol. 10878, pp. 183-192). SPIE.*

Zhu Y, Xu G, Yuan J, Jo J, Gandikota G, Demirci H, Agano T, Sato N, Shigeta Y, Wang X. Light emitting diodes based photoacoustic imaging and potential clinical applications. Scientific reports. Jun. 29, 2018;8(1):1-2.*

International Search Report and Written Opinion for PCT/EP2021/076422; Mailing date: Dec. 6, 2021, 10 pages.

Krizhevsky, A. et al., "ImageNet Classification with Deep Convolutional Neural Networks", NIPS, 2012, 9 pages.

Feigin, M. et al., "A Deep Learning Framework for Single-Sided Sound Speed Inversion in Medical Ultrasound", IEEE Trans Biomed Eng., 2020, vol. 67, No. 4, pp. 1142-1151.

Anonymous, "How To Read An Airport Security X-Ray Image", retrieved from http://snallabolaget.com/how-to-read-an-airport-security-x-ray-image/, 2010, 3 pages.

Anonymous, "The Visible Human Project", NIH, National Library of Medicine, 2019, 3 pages.

Aguilar, L. et al., "Famus II: A Fast and Mechanistic Ultrasound Simulator Using an Impulse Response Approach", IEEE Trans Ultrason Ferroelectr Freq Control., 2017, vol. 64, vol. 2, pp. 362-373.

* cited by examiner

| Tissue | Density ρ (kg m⁻³) | Velocity of sound c (m s⁻¹) | Attenuation coefficient $\alpha = af^b$ | | | Nonlinearity parameter B/A |
|---|---|---|---|---|---|---|
| | | | α (10² neper m⁻¹) | a (10² neper m⁻¹ MHz⁻ᵇ) | b | |
| Amniotic fluid | 965 | 1534 | 0.0093 @ 5 MHz | - | - | - |
| Blood | 1055 | 1584 | 0.095 @ 5 MHz | 0.14-0.018 | 1.19-1.23 | 6.0 |
| Bone (skull) | 1610 | 2190-3289 | 9.0 @ 3 MHz | - | - | - |
| Bone (trabecular) | 1920 | 1688-2407 | 0.22-1.8 @ 0.2-1.0 MHz | - | - | - |
| Brain | 1030-1041 | 1562 | 0.46-0.72 @ 5 MHz | 0.067-0.069 | 1.20-1.46 | 6.5-7.6 |
| Breast | 1020 | 1430-1570 | 0.96 @ 5 MHz | 0.086 | 1.5 | - |
| Eye (lens) | 1034-1113 | 1640-1673 | 0.9 @ 10 MHz | - | - | - |
| Eye (vitreous humor) | 1009 | 1523-1532 | 0.07 @ 6 MHz | - | - | - |
| Fat | 917-939 | 1412-1487 | 0.56 @ 6 MHz | - | - | 9.6-10.3 |
| Heart | 1044⁺ | 1571⁺ | 0.23 @ 1 MHz | - | - | 6.8 |
| Kidney | 1050 | 1560-1580 | 0.23 @ 2 MHz | - | - | 5.8-9.0 |
| Liver | 1050-1070 | 1578-1640 | 0.17-0.57 @ 5 MHz | 0.041-0.070 | 0.9-1.30 | 5.5-7.6 |
| Muscle (skeletal) | 1038-1056 | 1529-1629 | 0.54 @ 4.3 MHz | - | - | 7.4-8.1 |
| Pancreas | 1040-1050 | 1591 | 0.42 @ 5 MHz | 0.12 | 0.78 | - |
| Skin (epidermis) | 1110-1190 | 1729⁺ | 1.06 @ 5 MHz | - | - | 7.9 |
| Spleen | 1054 | 1567-1635 | 0.23-0.66 @ 5 MHz | 0.036-0.062 | 1.14-1.47 | 7.8 |
| Teeth (dentine) | 2030-2350 | 3140-4140 | 9.2 @ 18 MHz | - | - | - |
| Teeth (enamel) | 2890-3020 | 4500-6250 | 14.0 @ 18 MHz | - | - | - |
| Testes | 1044 | 1595 | 0.3 @ 5 MHz | 0.02 | 1.7 | - |
| Uterus | 1052 | 1629⁺ | 0.027-0.22⁺ @ 1 MHz | - | - | - |

RENDERING OF B-MODE IMAGES BASED ON TISSUE DIFFERENTIATION

CROSS-REFERENCE TO PRIOR APPLICATIONS

This application is the U.S. National Phase application under 35 U.S.C. § 371 of International Application No. PCT/EP2021/076422, filed on Sep. 26, 2021, which claims the benefit of U.S. Provisional Patent Application No. 63/084,870, filed on Sep. 29, 2020. This application is hereby incorporated by reference herein.

TECHNICAL FIELD

This application relates to generating color images from grayscale images. More specifically, this application relates to generating enhanced renderings from B-mode ultrasound images, enhanced, for example, based on the tissue type.

BACKGROUND

B-mode ultrasound imaging has been used to generate grayscale images since its introduction several decades ago. However, as advances in image processing have occurred in other imaging modalities, users have begun to demand more colorful and/or realistic images from B-mode imaging. In some applications, color and/or other visualization improvements may make B-mode images easier to interpret. As use of ultrasound imaging increases among non-experts (e.g., non-radiologists, non-sonographers, inexperienced sonographers), the need for easier image interpretation also increases.

SUMMARY

As disclosed herein, realistic rendering techniques based on tissue type and/or mechanical properties may be applied in lieu of grayscale mapping of B-mode images. Different tissue types (e.g., muscle, fat, liver, kidney) may be represented with different colors and/or other material properties that may make the tissue types appear more realistic and/or may make the tissue types easier to differentiate and/or interpret. In some examples, the different tissue types may be determined based on multiparametric imaging (e.g., attenuation, speed of sound, elastography). In some examples, other or additional techniques may be used to determine tissue type such as neural networks, B-mode texture, and/or anatomical models. The color and/or other material properties may be applied by using different rendering "recipes" for each tissue type. For example, tissue identified as fat may be assigned a white color and material properties that make the fat appear flat or matte and tissue identified as healthy liver may be assigned a red color and material properties that make the liver appear shiny.

In accordance with at least one example disclosed herein, an apparatus may include a processor configured to receive a B-mode image of an imaged volume, wherein the B-mode image comprises a plurality of first voxels, each associated with a different spatial location in the imaged volume and each comprising an intensity value corresponding to an intensity of echo signals received from the associated spatial location in the imaged volume, receive a tissue parameter map comprising one or more tissue parameter values for each of the plurality of first voxels, generate a 3D rendering dataset comprising a plurality of second voxels by assigning one or more material property values to each of the plurality of second voxels, wherein the one or more material property values assigned to each of the plurality of second voxels is based, at least in part, on the intensity value associated with the respective first voxel of the B-mode image, and further based, at least in part, on a tissue parameter value associated with the respective voxel obtained from the tissue parameter map, and generate an enhanced B-mode rendering from the 3D rendering dataset. The apparatus may include a display configured to display the enhanced B-mode rendering.

In accordance with at least one example disclosed herein, a method may include receiving a B-mode image of an imaged volume, wherein the B-mode image comprises a plurality of first voxels, each associated with a different spatial location in the imaged volume and each comprising an intensity value corresponding to an intensity of echo signals received from the associated spatial location in the imaged volume, receiving a tissue parameter map comprising one or more tissue parameter values for each of the plurality of first voxels, assigning one or more material property values to each of a plurality of second voxels of a 3D rendering dataset, wherein the one or more material property values assigned to each of the plurality of second voxels is based, at least in part, on the intensity value associated with the respective first voxel of the B-mode image, and further based, at least in part, on a tissue parameter value associated with the respective voxel obtained from the tissue parameter map, and generating an enhanced B-mode rendering from the 3D rendering dataset.

In accordance with at least one example disclosed herein, a method may include segmenting a B-mode image to determine a tissue type for individual ones of a plurality of first voxels of the B-mode image, assigning one or more material property values to each of a plurality of second voxels of a 3D rendering dataset, wherein the one or more material property values are based, at least in part, on the tissue type, generating an enhanced B-mode rendering from the 3D rendering dataset, and displaying the enhanced B-mode rendering on a display.

DESCRIPTION

The following description of certain exemplary examples is merely exemplary in nature and is in no way intended to limit the disclosure or its applications or uses. In the following detailed description of examples of the present apparatuses, systems and methods, reference is made to the accompanying drawings which form a part hereof, and in which are shown by way of illustration specific examples in which the described apparatuses, systems and methods may be practiced. These examples are described in sufficient detail to enable those skilled in the art to practice the presently disclosed apparatuses, systems and methods, and it is to be understood that other examples may be utilized and that structural and logical changes may be made without departing from the spirit and scope of the present disclosure. Moreover, for the purpose of clarity, detailed descriptions of certain features will not be discussed when they would be apparent to those with skill in the art so as not to obscure the description of the present disclosure. The following detailed description is therefore not to be taken in a limiting sense, and the scope of the present apparatuses, systems and methods is defined only by the appended claims.

Photorealistic rendering techniques for ultrasound, such as the TrueVue system developed by Koninklijke Philips, have recently become commercially available. However, existing photorealistic rendering techniques are typically applied to three dimensional (e.g., volume) datasets and may not differentiate between tissue types. New ultrasound imaging and data analysis techniques have also been developed that can determine one or more parameters of tissue (e.g., speed of sound through the tissue, attenuation of ultrasound signals in the tissue, stiffness). However, in existing systems these parameters are typically presented separately from B-mode images or the parameters are colormapped and simply overlaid on the B-mode images.

Figure 1:
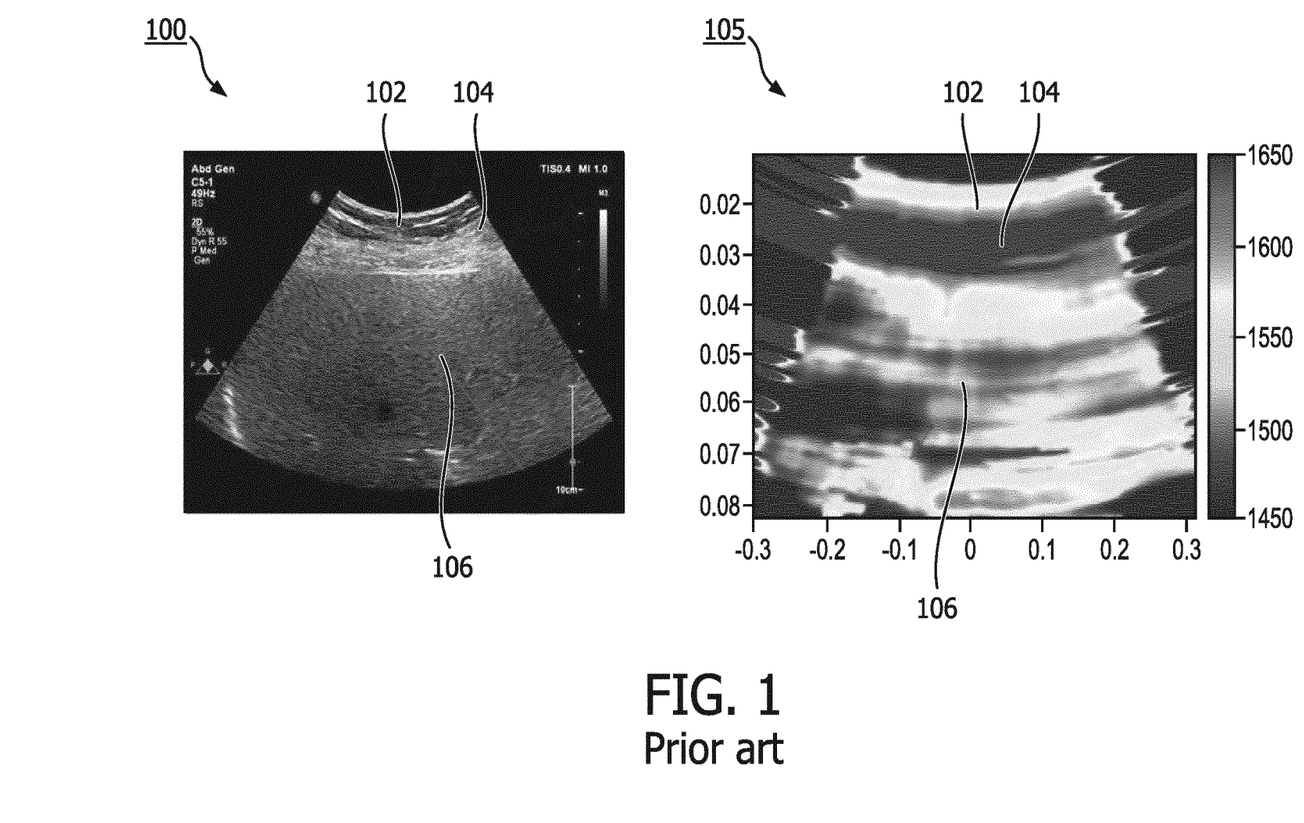
FIG. 1 shows an example of a B-mode image and a corresponding tissue parameter colormap.

FIG. 1 shows an example of a B-mode image and a corresponding tissue parameter colormap. The B-mode image 100 is a portion of a liver and surrounding tissue. The tissue parameter colormap 105 is a speed of sound map. In other words, the speed at which ultrasound signals travelled through the different regions of the tissue are mapped to different colors and displayed. In the B-mode image 100, the subcutaneous fat layer 102, underlying muscle layer 104, and liver tissue 106 present different textures and different pixel intensities. In the colormap 105, the subcutaneous fat layer 102 is bright blue indicating lower sound speeds, the muscle layer 104 is a deep red, indicating higher sound speeds, while the liver tissue 106 is light-to-dark blue, indicating even lower sound speeds. These stark variations in color make the different tissue types much easier to discern in the tissue parameter colormap 105. However, if the colormap 105 were to be overlaid onto the B-mode image 100, the structural and textural information provided by the B-mode image 100 would be obscured. Furthermore, the resolution of the colormap 105 is lower than that of the B-mode image 100, so an exact pixel-to-pixel (or voxel-to-voxel) correlation of the tissue types is not possible. For example, in principle, the fat layer 102 should have lower sound speeds than the liver tissue 106, but the fat layer 102 appears in the colormap 105 as having higher speeds due to averaging effects from the adjacent muscle layer 104.

According to examples of the present disclosure, multi-parametric ultrasound imaging may be used to determine different tissue types in B-mode images. In some examples, other or additional techniques may be used to determine tissue type such as neural networks, B-mode texture, and/or anatomical models. Pixels or voxels associated with different tissue types (e.g., muscle, fat, liver, kidney) may be assigned values for different colors and/or other material properties. Based on the values, a rendering, which may have the appearance of a color B-mode image, may be generated. The material properties assigned to the voxels may affect how the voxels are rendered (e.g., the appearance of the voxels in a rendering may vary with the material properties). The values for the colors and/or other material properties may allow the generation of a B-mode image where the tissue types appear more realistic and/or may make the tissue types easier to differentiate and/or interpret. In some examples, multiple parameters may be conveyed in the B-mode image, rather than requiring side-by-side views of B-mode images and parameter maps or overlaying of the parameter maps on the B-mode images.

Figure 2:
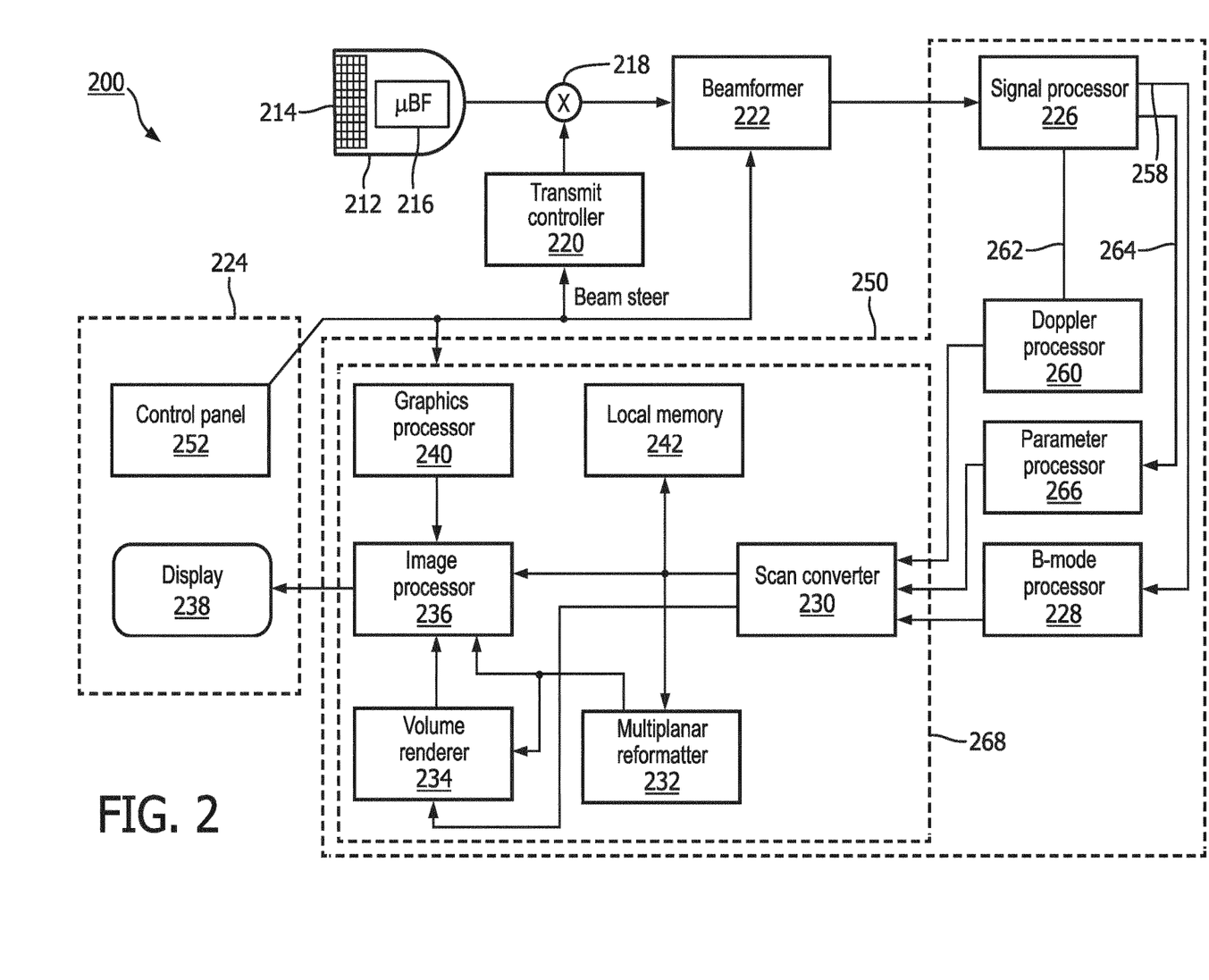
FIG. 2 is a block diagram of an ultrasound imaging system arranged in accordance with examples of the present disclosure.

FIG. 2 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as an intravascular ultrasound (IVUS) catheter probe. In other examples, the transducer array 214 may be in the form of a flexible array configured to be conformally applied to a surface of subject to be imaged (e.g., patient). The transducer array 214 is configured to transmit ultrasound signals (e.g., beams, waves) and receive echoes (e.g., received ultrasound signals) responsive to the transmitted ultrasound signals. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some examples, the transducer array 214 may be coupled to a microbeamformer 216, which may be located in the ultrasound probe 212, and which may control the transmission and reception of signals by the transducer elements in the array 214. In some examples, the microbeamformer 216 may control the transmission and reception of signals by active elements in the array 214 (e.g., an active subset of elements of the array that define the active aperture at any given time).

In some examples, the microbeamformer 216 may be coupled, e.g., by a probe cable or wirelessly, to a transmit/receive (T/R) switch 218, which switches between transmission and reception and protects the main beamformer 222 from high energy transmit signals. In some examples, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 214 under control of the microbeamformer 216 is directed by the transmit controller 220, which may be coupled to the T/R switch 218 and a main beamformer 222. The transmit controller 220 may control the direction in which beams are steered. Beams may be steered straight ahead from (orthogonal to) the transducer array 214, or at different angles for a wider field of view. The transmit controller 220 may also be coupled to a user interface 224 and receive input from the user's operation of a user input device (e.g., user control). The user interface 224 may include one or more input devices such as a control panel 252, which may include one or more mechanical controls (e.g., buttons, sliders, etc.), touch sensitive controls (e.g., a trackpad, a touchscreen, or the like), and/or other known input devices.

In some examples, the partially beamformed signals produced by the microbeamformer 216 may be coupled to a main beamformer 222 where partially beamformed signals from individual patches of transducer elements may be combined into a fully beamformed signal. In some examples, microbeamformer 216 is omitted. In these examples, the transducer array 214 is under the control of the main beamformer 222, and the main beamformer 222 performs all beamforming of signals. In examples with and without the microbeamformer 216, the beamformed signals of the main beamformer 222 are coupled to processing circuitry 250, which may include one or more processors (e.g., a signal processor 226, a B-mode processor 228, a Doppler processor 260, and one or more image generation and processing components 268) configured to produce an ultrasound image from the beamformed signals (i.e., beamformed RF data).

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and electronic noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 258 which couples the signals from the signal processor 226 to a B-mode processor 228 for producing B-mode image data.

The B-mode processor 228 can employ amplitude detection for the imaging of structures in the body. The B-mode processor 228 may generate signals for tissue images and/or contrast images. The signals produced by the B-mode processor 228 may be coupled to a scan converter 230 and/or a multiplanar reformatter 232. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format.

In some examples, the system may include a Doppler signal path 262 which couples the output from the signal processor 226 to a Doppler processor 260. The Doppler processor 260 may be configured to estimate the Doppler shift and generate Doppler image data. The Doppler image data may include color data which is then overlaid with B-mode (i.e. grayscale) image data for display. The Doppler processor 260 may be configured to filter out unwanted signals (i.e., noise or clutter associated with non-moving tissue), for example using a wall filter. The Doppler processor 260 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function (e.g., R1) and Doppler power estimation is based on the magnitude of the lag-zero autocorrelation function (e.g., R0). The velocity estimations may be referred to as color Doppler data and the power estimations may be referred to as power Doppler data. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates (e.g., the color and power Doppler data) may undergo further threshold detection to further reduce noise, as well as segmentation and post-processing such as filling and smoothing. The velocity and/or power estimates may then be mapped to a desired range of display colors and/or intensities in accordance with one or more color and/or intensity maps. The map data, also referred to as Doppler image data, may then be coupled to the scan converter 230, where the Doppler image data may be converted to the desired image format to form a color Doppler or a power Doppler image.

In some embodiments, the system 200 may include a parameter imaging signal path 264 which couples the signals from the signal processor 226 to a parameter processor 266 for producing tissue parameter measurements. The parameter processor 266 may produce one or more types of tissue parameter measurements. In some examples, the tissue parameter measurements may be mapped to pixel or voxel color and/or intensity values to generate maps (e.g., stiffness maps, speed of sound maps) that may be overlaid onto B-mode and/or Doppler images. In some examples, the scan converter 230 may align the tissue parameter measurements with the B-mode and/or Doppler images.

The multiplanar reformatter 232 can convert echoes which are received from points in a common plane (e.g., slice) in a volumetric region of the body into an ultrasonic image (e.g., a B-mode image) of that plane, for example as described in U.S. Pat. No. 6,443,896 (Detmer). In some examples, the user interface 224 may be coupled to the multiplanar reformatter 232 for selection and control of a display of multiple multiplanar reformatted (MPR) images. In other words, a user may select a desired plane within the volume from which to generate a 2D image. In some examples, in addition to selecting a location and/or orientation of the plane in the volume, the user may also select a thickness of the plane. In some examples, the plane data of the multiplanar reformatter 232 may be provided to a volume renderer 234.

The volume renderer 234 may generate an image (also referred to as a projection, 3D scene, or rendering) of the 3D dataset as viewed from a given reference point, for example as described in U.S. Pat. No. 6,530,885 (Entrekin et al.). In some examples, while the image generated by the volume renderer 234 is based on a volume (e.g., 3D data set), which may include voxels, the final image rendered by the volume renderer 234 may be a 2D dataset (e.g., 2D image) that includes pixels. The 2D image may then be displayed on a conventional display (e.g., liquid crystal display).

According to examples of the present disclosure, the volume renderer 234 may receive a 2D and/or a 3D B-mode image from the scan converter 230 and/or the multiplanar reformatter 232. The 2D image includes a 2D dataset including pixels with intensity values. The 3D image includes a 3D dataset including voxels with intensity values.

In some examples, the volume renderer 234 may transform the 2D dataset into a 3D dataset as is described in more detail in European Patent Application No. 20290062.7 entitled "RENDERING OF TWO DIMENSIONAL DATA SETS" filed on Aug. 20, 2020. In other examples, the volume renderer 234 may transform the 2D dataset into a single layer of voxels having intensity values corresponding to the intensity values of the pixels. The volume renderer 234 may receive tissue parameter measurements that correspond to the 2D or 3D image from the scan converter 230 and/or multiplanar reformatter 232. In some examples, the volume renderer 234 may assign material properties (e.g., color, absorption, scattering) to each voxel in the 3D dataset based, at least in part, on the tissue parameter measurements. The volume renderer 234 may generate a rendering (e.g., an enhanced B-mode rendering) based, at least in part, on the material properties assigned to the voxels. The volume renderer 234 may simulate at least one light source when generating the rendered image in some examples.

In some examples, the volume renderer 234 may apply other segmentation techniques such as B-mode texture analysis, anatomical models, and/or artificial intelligence/machine learning (e.g., neural networks) to differentiate between tissue types. The volume renderer 234 may assign the material properties to the voxels based, at least in part, on the tissue types determined by the other segmentation techniques. In some cases, when other segmentation techniques are used, the volume renderer 234 may not use the tissue parameter measurements and/or the parameter processor 266 may be omitted. In some cases, other segmentation techniques may be used to supplement and/or enhance the tissue parameter measurements for assigning material properties to the voxels. For example, the resolution of the tissue parameter measurements may be increased to more closely match the resolution of the B-mode image.

Output from the scan converter 230 (e.g., B-mode images, Doppler images), the multiplanar reformatter 232, and/or the volume renderer 234 (e.g., renderings, 3D scenes) may be coupled to an image processor 236 for further enhancement, buffering and temporary storage before being displayed on an image display 238. In some examples, a Doppler image may be overlaid on a B-mode image of the tissue structure by the scan converter 230 and/or image processor 236 for display.

A graphics processor 240 may generate graphic overlays for display with the images. These graphic overlays may contain, for example, standard identifying information such as patient name, date and time of the image, imaging parameters, and the like. For these purposes the graphics processor 240 may be configured to receive input from the user interface 224, such as a typed patient name or other annotations The system 200 may include local memory 242. Local memory 242 may be implemented as any suitable non-transitory computer readable medium (e.g., flash drive, disk drive). Local memory 242 may store data generated by the system 200 including images, anatomical models, rendering "recipes," executable instructions, inputs provided by a user via the user interface 224, or any other information necessary for the operation of the system 200.

As mentioned previously system 200 includes user interface 224. User interface 224 may include display 238 and control panel 252. The display 238 may include a display device implemented using a variety of known display technologies, such as LCD, LED, OLED, or plasma display technology. In some examples, display 238 may comprise multiple displays. The control panel 252 may be configured to receive user inputs (e.g., desired image plane, desired light source, etc.). The control panel 252 may include one or more hard controls (e.g., buttons, knobs, dials, encoders, mouse, trackball or others). In some examples, the control panel 252 may additionally or alternatively include soft controls (e.g., GUI control elements or simply, GUI controls) provided on a touch sensitive display. In some examples, display 238 may be a touch sensitive display that includes one or more soft controls of the control panel 252.

In some examples, various components shown in FIG. 2 may be combined. For instance, image processor 236 and graphics processor 240 may be implemented as a single processor. In another example, the Doppler processor 260 and B-mode processor 228 may be implemented as a single processor. In some examples, various components shown in FIG. 2 may be implemented as separate components. For example, signal processor 226 may be implemented as separate signal processors for each imaging mode (e.g., B-mode, Doppler). In some examples, one or more of the various processors shown in FIG. 2 may be implemented by general purpose processors and/or microprocessors configured to perform the specified tasks. In some examples, one or more of the various processors may be implemented as application specific circuits. In some examples, one or more of the various processors (e.g., image processor 236) may be implemented with one or more graphical processing units (GPU).

Figure 3:
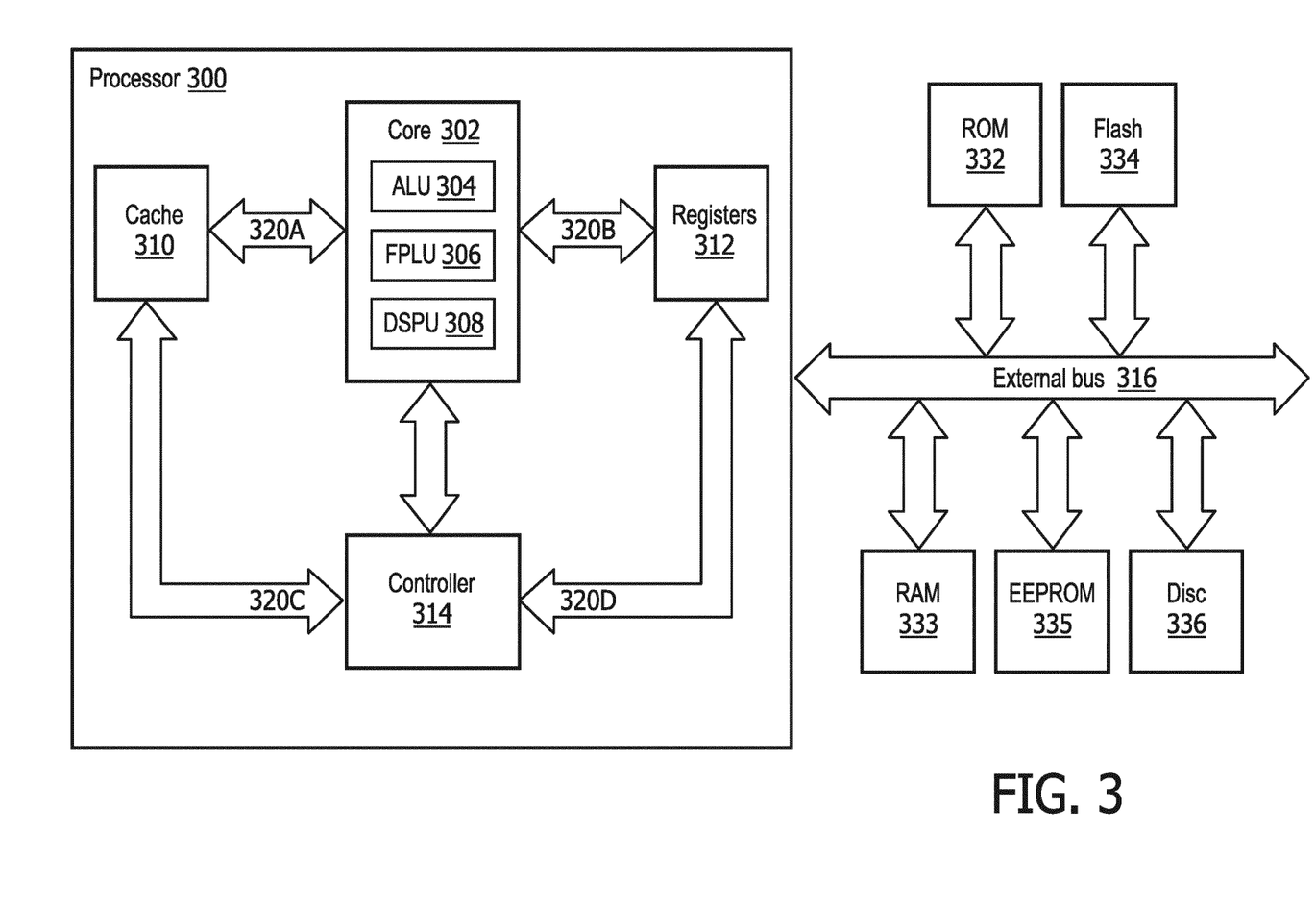
FIG. 3 is a block diagram illustrating an example processor in accordance with examples of the present disclosure.

FIG. 3 is a block diagram illustrating an example processor 300 according to principles of the present disclosure. Processor 300 may be used to implement one or more processors described herein, for example, image processor 236 shown in FIG. 2. Processor 300 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 300 may include one or more cores 302. The core 302 may include one or more arithmetic logic units (ALU) 304. In some examples, the core 302 may include a floating point logic unit (FPLU) 306 and/or a digital signal processing unit (DSPU) 308 in addition to or instead of the ALU 304.

The processor 300 may include one or more registers 312 communicatively coupled to the core 302. The registers 312 may be implemented using dedicated logic gate circuits (e.g., flip-flops) and/or any memory technology. In some examples the registers 312 may be implemented using static memory. The register may provide data, instructions and addresses to the core 302.

In some examples, processor 300 may include one or more levels of cache memory 310 communicatively coupled to the core 302. The cache memory 310 may provide computer-readable instructions to the core 302 for execution. The cache memory 310 may provide data for processing by the core 302. In some examples, the computer-readable instructions may have been provided to the cache memory 310 by a local memory, for example, local memory attached to the external bus 316. The cache memory 310 may be implemented with any suitable cache memory type, for example, metal-oxide semiconductor (MOS) memory such as static random access memory (SRAM), dynamic random access memory (DRAM), and/or any other suitable memory technology.

The processor 300 may include a controller 314, which may control input to the processor 300 from other processors and/or components included in a system (e.g., control panel 252 and scan converter 230 shown in FIG. 2) and/or outputs from the processor 300 to other processors and/or components included in the system (e.g., display 238 and volume renderer 234 shown in FIG. 2). Controller 314 may control the data paths in the ALU 304, FPLU 306 and/or DSPU 308. Controller 314 may be implemented as one or more state machines, data paths and/or dedicated control logic. The gates of controller 314 may be implemented as standalone gates, FPGA, ASIC or any other suitable technology.

The registers 312 and the cache memory 310 may communicate with controller 314 and core 302 via internal connections 320A, 320B, 320C and 320D. Internal connections may implemented as a bus, multiplexor, crossbar switch, and/or any other suitable connection technology.

Inputs and outputs for the processor 300 may be provided via a bus 316, which may include one or more conductive lines. The bus 316 may be communicatively coupled to one or more components of processor 300, for example the controller 314, cache memory 310, and/or register 312. The bus 316 may be coupled to one or more components of the system, such as display 238 and control panel 252 mentioned previously.

The bus 316 may be coupled to one or more external memories. The external memories may include Read Only Memory (ROM) 332. ROM 332 may be a masked ROM, Electronically Programmable Read Only Memory (EPROM) or any other suitable technology. The external memory may include Random Access Memory (RAM) 333. RAM 333 may be a static RAM, battery backed up static RAM, Dynamic RAM (DRAM) or any other suitable technology. The external memory may include Electrically Erasable Programmable Read Only Memory (EEPROM) 335. The external memory may include Flash memory 334. The external memory may include a magnetic storage device such as disc 336. In some examples, the external memories may be included in a system, such as ultrasound imaging system 200 shown in FIG. 2, for example local memory 242.

The functions performed by a volume renderer, such as volume renderer 234, to generate renderings from B-mode imaging and/or multiparametric imaging in accordance with examples of the present disclosure will now be described in more detail with reference to the following figures.

Figure 4:
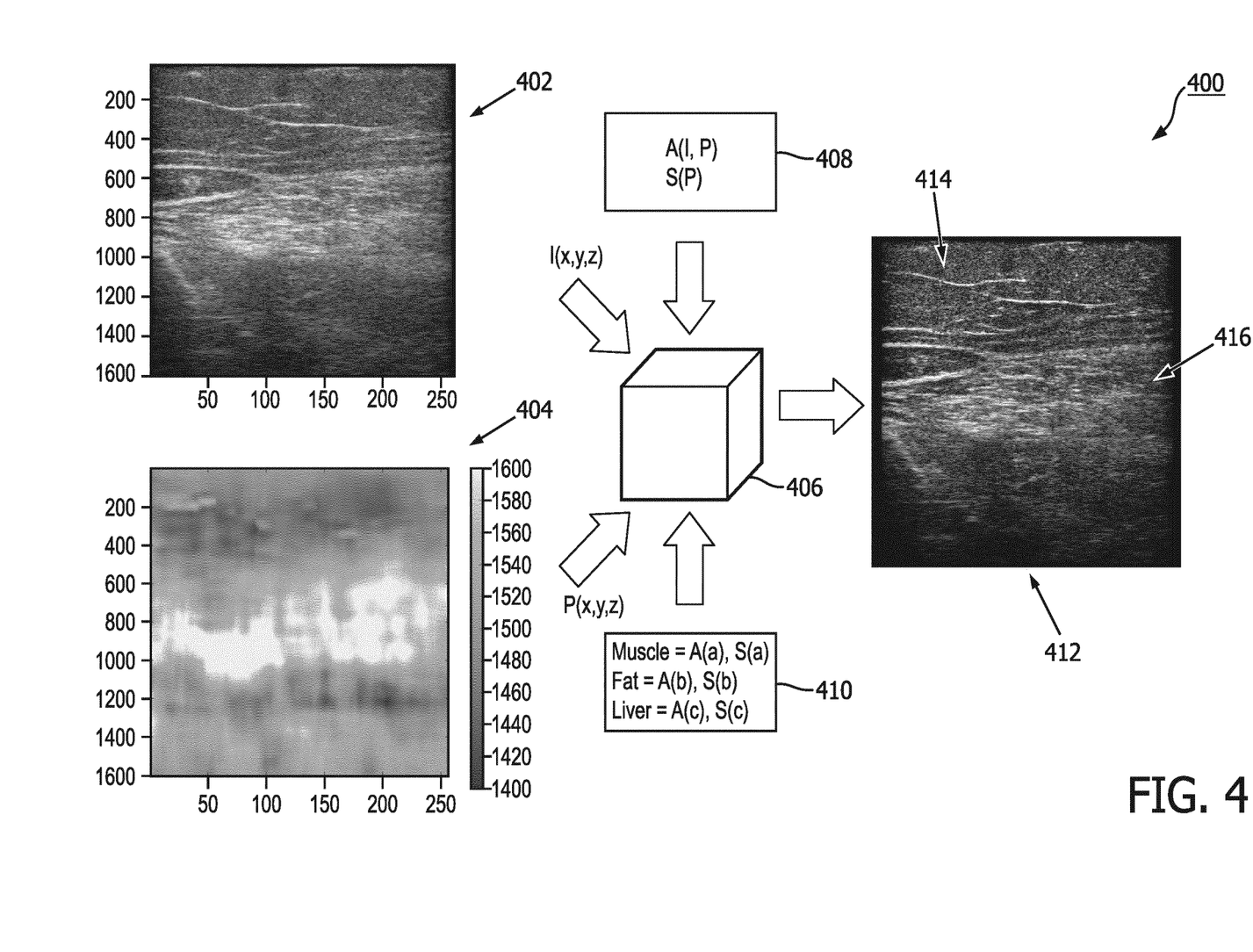
FIG. 4 shows a graphical representation of a process of generating a rendering from B-mode and multiparametric imaging in accordance with examples of the present disclosure.

FIG. 4 shows a graphical representation of a process of generating a rendering from B-mode and multiparametric imaging in accordance with examples of the present disclosure, which may be implemented or embodied in one or more of the processors, such as the volume rendered 234, image processor 236, or combinations thereof of the ultrasound imaging system 200. A volume B-mode image 402 and a volume tissue parameter map 404 may be received by a processor (e.g., volume renderer 234). In the example shown in FIG. 4, both the B-mode image 402 and tissue parameter map 404 are 3D datasets. In some examples, the datasets may have been 2D datasets converted into 3D datasets as described with reference to FIG. 2. In some examples, the datasets may have originally been 3D datasets. In some examples, the B-mode image 402 may include a volume data set of intensity values I(x,y,z) assigned to the voxels. An intensity value may correspond to an intensity of echo signals received from a spatial location in an imaged volume associated with a voxel. Each voxel may correspond to a different spatial location in the imaged volume. The tissue parameter map 404 may include a volume data set of tissue parameter values P(x,y,z). In some examples, the tissue parameter map 404 may include values for multiple parameters (e.g., density, velocity of sound, attenuation) for each voxel of the dataset. Each voxel may correspond to a different spatial location in the scanned volume. In some examples, there may be a one-to-one correspondence between the voxels of the B-mode image 402 and the tissue parameter map 404.

In some examples, the B-mode image 402 and the tissue parameter map 404 may have been acquired from a same volume in a subject. The B-mode image 402 and tissue parameter map 404 may have been acquired during a same acquisition. In other words, the B-mode image 402 and the tissue parameter map 404 may have been generated from signals based on echoes received by a transducer array (e.g., transducer array 214), where the echoes were responsive to a same set of transmitted ultrasound signals. In other examples, the B-mode image 402 and the tissue parameter map 404 may have been acquired during different acquisitions. For example, this may occur when one or more of the tissue parameters of interest require different acquisition settings (e.g., different frequency, pulse width, pulse duration, etc) than B-mode signals.

The processor may generate a 3D rendering data set including voxels 406 by assigning one or more material properties to voxels 406 based on the B-mode image 402 and tissue parameter map 404. In some examples, there may be a voxel 406 that corresponds to every voxel in the B-mode image 402.

In some examples, as shown in box 408, the processor may assign values for one or more material properties based on a function of the B-mode image 402 and/or the tissue parameter map 404. For example, a material property may be a function of the intensity I and/or tissue parameter values P. In the example shown, two material properties, absorption A and scattering S, are shown, but more or fewer material properties may be assigned values in other examples. Continuing with the example, absorption may be based on a function of both the intensity from the B-mode image 402 and the tissue parameter values from the tissue parameter map 404 and the scattering may be based on a function of the tissue parameter values from the tissue parameter map 404. However, this is provided only as an example and in other examples, all material properties may be functions of both the B-mode image 402 and the tissue parameter map 404 or some material properties may be functions solely of the B-mode image 402. In some examples, the material properties are defined by transfer functions based on the intensity and/or tissue parameter values.

Figure 5:
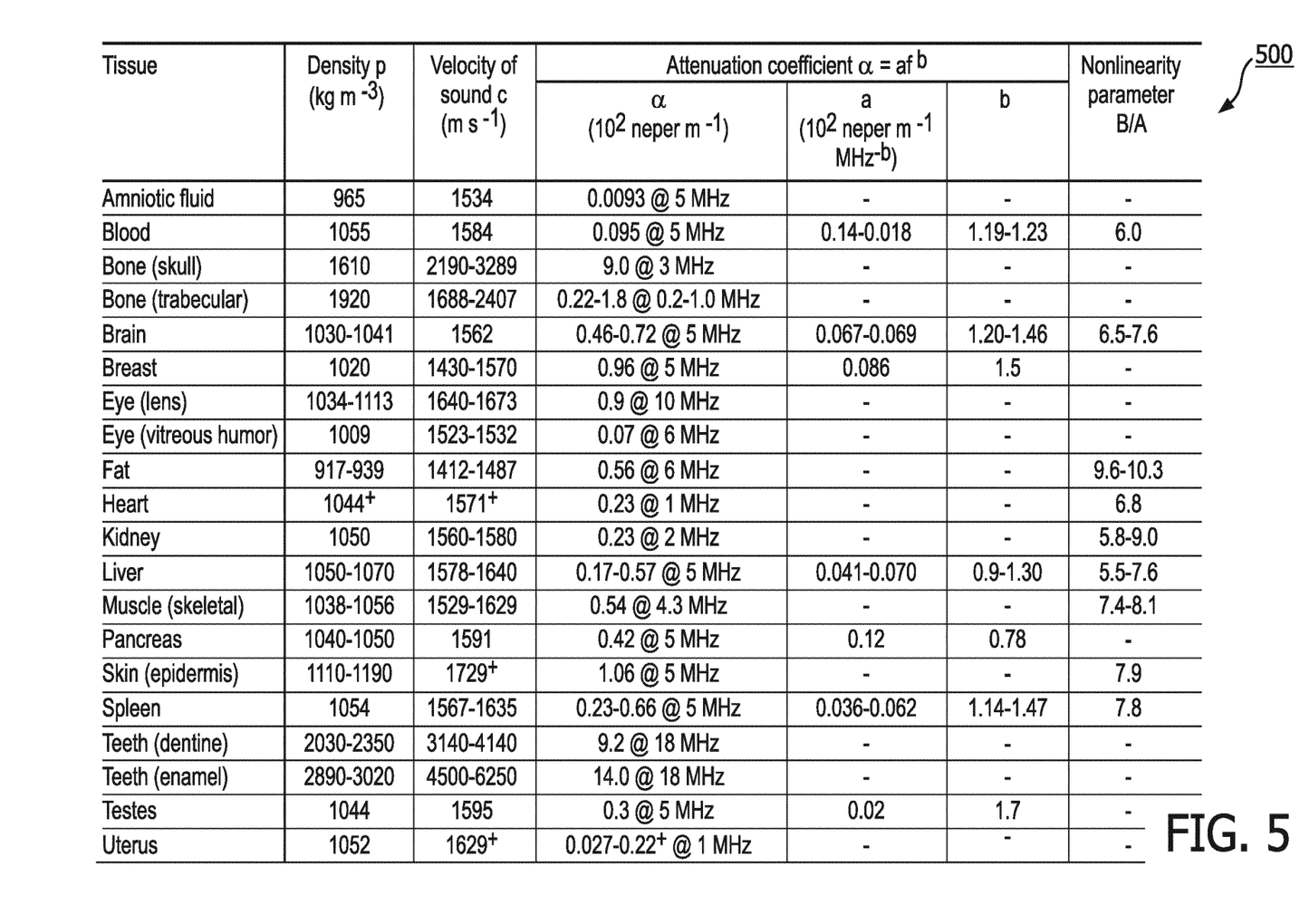
FIG. 5 is an example of a tissue parameter table.

In some examples, as shown in box 410, the processor may analyze the tissue parameter values from the tissue parameter map 404 to determine the tissue type at each voxel 406. In some examples, the tissue parameter values may be compared to a table to determine the tissue type. An example of a tissue parameter table 500, which may be accessed by the processor (e.g., volume renderer 234) is shown in FIG. 5. In some examples, the B-mode image 402 may also be analysed to determine the tissue type. Once the tissue type has been determined, the processor may assign material property values based on a profile for the particular tissue type. By profile, it is meant that the material properties assigned to the voxel 406 for the tissue type are predetermined rather than directly calculated (e.g., as described with reference to box 408) based on the tissue parameters. In the example shown in FIG. 4, the profiles include values for absorption and scattering. Of course, fewer or additional material properties may be included in the profiles. Furthermore, although only three tissue types are shown in box 410, profiles for more or fewer tissue types may be included.

Applying material properties based on functions of the intensity and/or tissue parameters (e.g., as shown in box 408) rather than based on predetermined profiles (e.g., as shown in box 410) may be preferred in some applications when one or more tissue parameters (e.g., stiffness, attenuation) are to be conveyed in an enhanced rendering as well as information about the anatomical structures being imaged (e.g., B-mode image data). For example, the material properties may be assigned such that fat tissue is rendered in a different color than liver tissue, which may make it easier for a user to differentiate fat tissue from liver tissue. In the same example, voxels associated with liver tissue may also be assigned different intensity values and/or "shininess" values based on measured stiffness values. Thus, while the liver tissue voxels may have the same color, different portions of the liver may look dimmer and/or duller based, at least in part, on the stiffness values. However, applying predetermined profiles based on tissue type as described with reference to box 410 may use less computational power and/or avoid confusing a user with extraneous information when the actual tissue parameter values are of little to no interest to the user.

In some examples, values for material properties may be assigned based on a combination of predetermined profiles and functions of intensity and/or tissue parameters. For example, a tissue type of a voxel 406 may be determined based on the intensity and/or tissue parameters. Based on the tissue type, a corresponding profile of material properties may be used to assign values for some of the material properties. However, one or more of the material properties may not have a predetermined value and may be assigned based on a function of the intensity and/or tissue parameter values. In some examples, the function to use for the material property may be stored in the profile for the tissue type.

Once material properties have been assigned to the voxels 406, the processor (e.g., volume renderer 243) may generate a rendering 412 from the voxels 406. In some examples, the rendering 412 may be shown on a display, such as display 238. As will be described in more detail with reference to FIG. 8, the processor may generate the rendering 412 using a two-step rendering process in some examples. In the example shown in FIG. 4, the B-mode image 402 is of a portion of a leg and the tissue parameter map 404 shows the corresponding speed of sound in tissue values. In the rendering 412, an upper layer of fat 414 and a lower layer of muscle 416 can be discerned more easily than in the B-mode image 402. However, unlike when the tissue parameter map 404 is merely overlaid on the B-mode image 402, the details of the B-mode image 402 are not lost in rendering 412.

Figure 6:
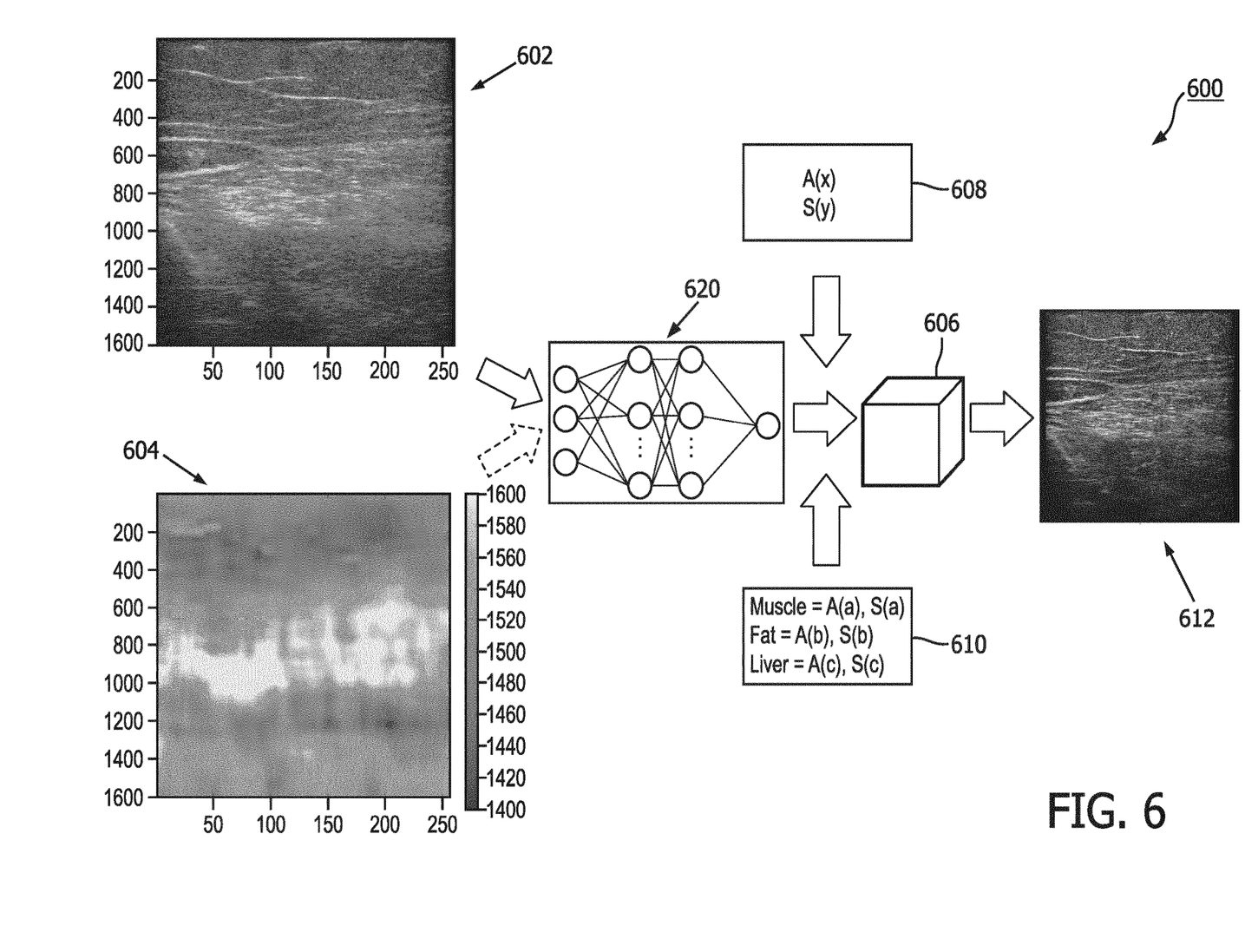
FIG. 6 shows a graphical representation of a process of generating a rendering from B-mode imaging in accordance with examples of the present disclosure.

FIG. 6 shows a graphical representation of a process of generating a rendering from B-mode imaging in accordance with examples of the present disclosure. A volume B-mode image 602 may be received by a processor (e.g., volume renderer 234). In some examples, and a volume tissue parameter map 604 may also be received by the processor. The B-mode image 602 and the tissue parameter map 604 may be substantially the same as B-mode image 402 and tissue parameter map 404.

In the example shown in FIG. 6, the processor (e.g., volume renderer 234, image processor, or another or any combinations thereof) may apply one or more image segmenting techniques to the B-mode image 602 and/or tissue parameter map 604 to determine the material properties to assign for each voxel. As shown in box 620, the processor may implement or communicate with a neural network to determine the material properties. However, other artificial intelligence or machine learning techniques may be used. Training of an AI/machine learning model to perform segmentation is described in more detail in reference to FIG. 7. Other non-AI/machine learning techniques may also be used such as edge detection, B-mode texture analysis, and/or anatomic modelling (an example of which may be found in U.S. Pat. No. 7,957,572). These other techniques may be used instead of or in addition to the AI/machine learning techniques. Based on the segmentation, the processor may then assign one or more material properties to voxels 606 of a volume dataset. In some examples, the volume data set may have a voxel that corresponds to every voxel in the B-mode image 602.

In some examples, as shown in box 608, the processor (e.g., volume renderer 234) may assign values for one or more material properties based on functions of the segmenting technique used, similar to the example described with reference to box 408 shown in FIG. 4. In the example shown, two material properties, absorption A and scattering S, are shown, but more or fewer material properties may be assigned values in other examples. For example, the output of a neural network or other segmentation technique performed at box 620 may be a set of material property values for each voxel 606. In some examples, as shown in box 610, the segmentation may determine the tissue type at each voxel 606. For example, the output of a machine learning model may be the tissue type for each voxel 606. Once the tissue type is determined, the processor may apply tissue-type specific profiles of material properties to the voxels 606, similar to the example described with reference to box 410 shown in FIG. 4. In some examples, values for material properties may be assigned based on a combination of predetermined profiles and outputs from the segmentation shown in box 620. For example, a tissue type of a voxel 606 may be determined based on the segmentation. Based on the tissue type, a corresponding profile of material properties may be used to assign values for some of the material properties. However, one or more of the material properties may not have a predetermined value and may be assigned based on a separate output of the segmentation illustrated in box 620. Once material properties have been assigned to the voxels 606, the volume renderer may generate an enhanced B-mode rendering 612 from the voxels 606 in the same manner as described with reference to FIG. 4.

In some examples, such as those described in reference to FIG. 6, to perform image segmentation, a processor (e.g., volume renderer 234) may include any one or more machine learning models, artificial intelligence algorithms, and/or neural networks. In some examples, the processor (e.g., volume renderer 234, image processor 236 or another processor or combinations thereof) may include a deep neural network (DNN), a convolutional neural network (CNN), a recurrent neural network (RNN), an autoencoder neural network, or the like, to determine the material properties of voxels and/or determine a tissue type of voxels. The model and/or neural network may be implemented in hardware (e.g., neurons are represented by physical components) and/or software (e.g., neurons and pathways implemented in a software application) components. The model and/or neural network implemented according to the present disclosure may use a variety of topologies and learning algorithms for training the model and/or neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a trained algorithm for determine the material properties of voxels and/or determine a tissue type of voxels. In some embodiments, the processor (e.g., volume renderer) may implement a model and/or neural network in combination with other image processing methods (e.g., segmentation, histogram analysis).

In various examples, the model(s) and/or neural network(s) may be trained using any of a variety of currently known or later developed learning techniques to obtain a model and/or neural network (e.g., a trained algorithm, transfer function, or hardware-based system of nodes) that is configured to analyze input data in the form of ultrasound images, measurements, and/or statistics. In some embodiments, the model and/or neural network may be statically trained. That is, the model and/or neural network may be trained with a data set and then deployed on an ultrasound system (e.g., system 200), for example in a processor such as the volume renderer 234. In some embodiments, the model and/or neural network may be dynamically trained. In these embodiments, the model and/or neural network may be trained with an initial data set and deployed on the ultrasound system. However, the model and/or neural network may continue to train and be modified based on ultrasound images acquired by the ultrasound system after deployment of the model and/or neural network on the ultrasound system.

Figure 7:
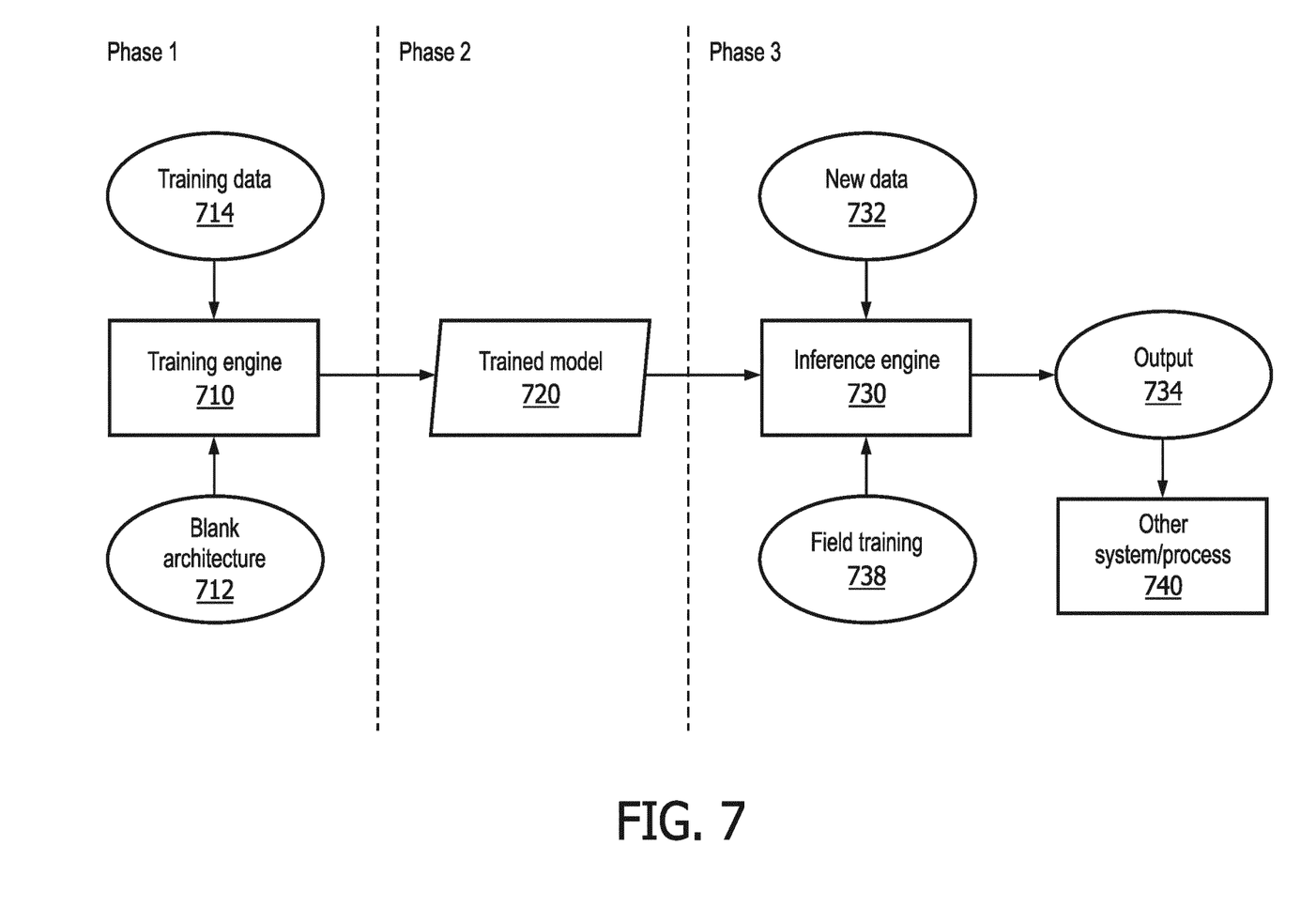
FIG. 7 shows a block diagram of a process for training and deployment of a model in accordance with examples of the present disclosure FIG. 8 provides a graphical overview of two-step rendering process in accordance with examples of the present disclosure.

FIG. 7 shows a block diagram of a process for training and deployment of a model in accordance with examples of the present disclosure. The process shown in FIG. 7 may be used to train a model (e.g., artificial intelligence, machine learning, deep learning) implemented by a processor of an ultrasound system (e.g., volume renderer 234). For example, the process shown in FIG. 7 may be used to train a model used to segment an image as shown in block 620 in FIG. 6.

The left hand side of FIG. 7, phase 1, illustrates the training of a model. To train the model, training sets which include multiple instances of input arrays and output classifications may be presented to the training algorithm(s) of the model(s) (e.g., AlexNet training algorithm, as described by Krizhevsky, A., Sutskever, I. and Hinton, G. E. "ImageNet Classification with Deep Convolutional Neural Networks," NIPS 2012 or its descendants). Training may involve the selection of a starting algorithm and/or network architecture 712 and the preparation of training data 714. The starting architecture 712 may be a blank architecture (e.g., an architecture with defined layers and arrangement of nodes but without any previously trained weights, a defined algorithm with or without a set number of regression coefficients) or a partially trained model, such as the inception networks, which may then be further tailored for analysis of ultrasound data. The starting architecture 712 (e.g., blank weights) and training data 714 are provided to a training engine 710 for training the model. Upon sufficient number of iterations (e.g., when the model performs consistently within an acceptable error), the model 720 is said to be trained and ready for deployment, which is illustrated in the middle of FIG. 7, phase 2. The right hand side of FIG. 7, or phase 3, the trained model 720 is applied (via inference engine 730) for analysis of new data 732, which is data that has not been presented to the model during the initial training (in phase 1). For example, the new data 732 may include unknown data such as live ultrasound images acquired during a scan of a patient (e.g., cardiac images during an echocardiography exam). The trained model 720 implemented via engine 730 is used to analyze the unknown data in accordance with the training of the model 720 to provide an output 734 (e.g., a tissue type, a material property value). The output 734 may then be used by the system for subsequent processes 740 (e.g., assigning material properties to voxels, generating a rendering).

In the embodiments where the trained model 720 is used as a model implemented or embodied by a processor of an ultrasound system (e.g., the volume renderer 234), the starting architecture may be that of a convolutional neural network, or a deep convolutional neural network in some examples, which may be trained to provide one or more material property values for a voxel and/or a tissue type of a voxel. The training data 714 may include multiple (hundreds, often thousands or even more) annotated/labeled images, also referred to as training images. For example, voxels of training images may be labelled with tissue types and/or material properties. It will be understood that the training image need not include a full image produced by an imaging system (e.g., representative of the full field of view of an ultrasound probe) but may include patches or portions of images.

In some examples, where insufficient ultrasound training data exists, images from other modalities (e.g., computed tomography, magnetic resonance imaging, even photographs, such as from the National Institute of Health's Visible Human Project) may be used as training data. In some examples, ultrasound data may be simulated from the images from other modalities using an ultrasound simulator, such as k-wave or FAMUS II. The simulated ultrasound data may be labelled then used as training data.

In some examples, labelled tissue parameter maps may also be provided as training data. In these examples, the model may be trained to segment images and/or assign material property values to voxels based on both a B-mode image and a tissue parameter map. In some examples, multiple types of tissue parameter maps may be provided as training data (e.g., speed of sound, attenuation, and stiffness maps).

In various embodiments, the trained model(s) may be implemented, at least in part, in a computer-readable medium comprising executable instructions executed by one or more processors of an ultrasound system, e.g., the volume renderer 234.

Figure 8:
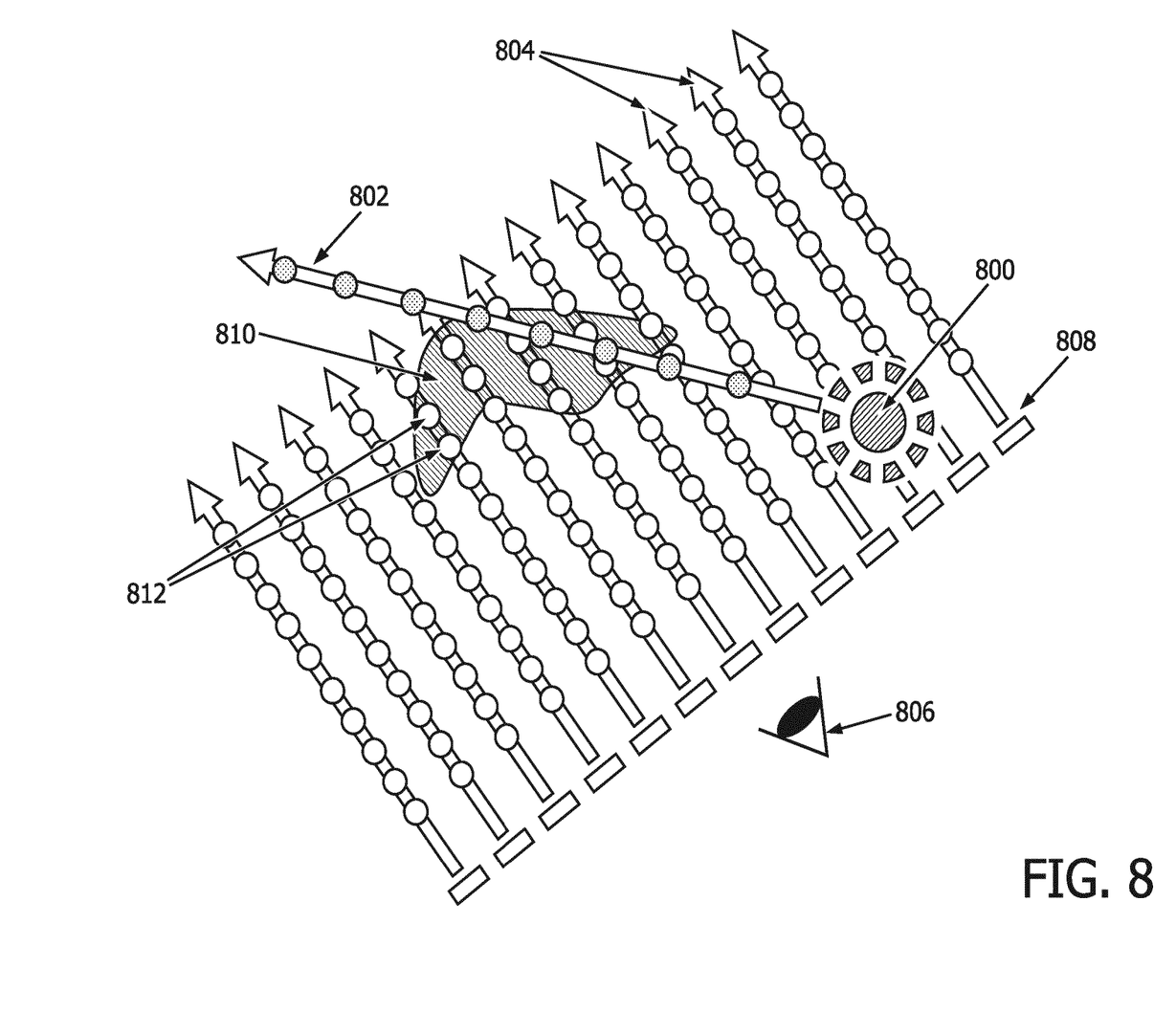

FIG. 8 provides a graphical overview of two-step rendering process in accordance with examples of the present disclosure. In some examples, the rendering process shown in FIG. 8 may be used to generate enhanced B-mode renderings, such as renderings 412 and/or 612. In some examples, a processor of an ultrasound system, such as volume renderer 234, may perform a lighting pass and a compositing pass to generate a rendering. In some examples, the lighting pass may be performed prior to the compositing pass. During the lighting pass, a virtual light source 800 is simulated in relation to a volume 810. Volume 810 may include voxels to which material properties have been assigned by the processor (e.g., volume renderer 234) based, at least in part, on a B-mode image. The material properties may have been assigned using the methods described with reference to FIGS. 4-6 in some examples. In some examples, such as the one shown in FIG. 6, the light source 800 may be a point light source that radiates light in all directions with equal intensity. In other examples, the light source 800 may be a directed light source (e.g., spotlight, beam). In some examples, multiple light sources may be simulated. The number of light sources, type of light source, position of the light source 800 relative to the volume 810 and/or the intensity of the light source 800 may be pre-set or selected by a user via a user interface. In some examples, other properties of the light source may also be selected by a user such as a size of the light source 800 and/or a color (e.g., wavelength range) of the light source 800. Examples of suitable light sources and user-control thereof may be found in U.S. patent application Ser. Nos. 16/306,951 and 16/347,739, the contents of which are incorporated herein by reference for any purpose.

Continuing with the lighting pass, light from the light source 800 is propagated in three dimensional space through the volume 810. In FIG. 8, only a single light ray 802 is shown, but it understood that many light rays are propagated through the volume 810 to simulate the light source 800. The amount of light reaching each voxel of the volume 810 is computed according to the properties of the light source 800 and the material properties assigned to each voxel. For example, certain voxels may have wavelength dependent absorption, which may cause the voxels to appear a certain color. For example, voxels determined to correspond to muscle tissue may absorb less at red wavelengths, causing those voxels to appear red in the final rendering. The computed amount of light for each voxel is stored for use in the compositing pass.

During the compositing pass, parallel rays 804 are propagated through the volume 810 from an observation plane 808 of a virtual observer 806. In some examples, the rays 804 may be orthogonal to the observation plane 808. The distance of the observation plane 808 from the volume 810 and/or the orientation of the observation plane 808 relative to the volume 810 may be pre-set or selected by a user via a user interface. In some examples, the processor (e.g., volume renderer 234) may implement a ray marching numerical scheme that uses a front-to-back red-green-blue (RGB) accumulation with tri-linear interpolated volumetric samples 812 along the direction of the rays 804. Based on the light calculated for each voxel in the lighting pass and the ray 804 marching, the processor (e.g., volume renderer 234) may compute a final value of the voxel and/or pixel of the rendering shown to the user on a display (e.g., display 238).

As disclosed herein, systems and methods using multi-parametric ultrasound imaging may be used to determine different tissue types in B-mode images and/or assign material properties to voxels. In some examples, other or additional techniques may be used to determine tissue type and/or assign material properties to voxels. Voxels may be assigned different values for colors, densities, scattering, and/or other material properties based, at least in part, on tissue type. Based on the material property values assigned to the voxels, a color B-mode image may be generated. B-mode images generated by the systems and methods disclosed herein may appear more realistic and/or may make tissue types easier to differentiate and/or interpret. In some examples, multiple parameters may be conveyed in the rendered B-mode image, rather than requiring a user to analyze separate images and parameter maps or obscuring the B-mode image with parameter maps.

In various examples where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present apparatuses, systems and methods may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, examples or processes described herein may be combined with one or more other examples, examples and/or processes or be separated and/or performed amongst separate devices or device portions in accordance with the present apparatuses, systems, devices and methods.

Finally, the above-discussion is intended to be merely illustrative of the present systems and methods and should not be construed as limiting the appended claims to any particular example or group of examples. Thus, while the present system has been described in particular detail with reference to exemplary examples, it should also be appreciated that numerous modifications and alternative examples may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. An apparatus comprising:
   a processor configured to:
      receive a B-mode image of an imaged volume, wherein the B-mode image comprises a plurality of first voxels, each associated with a different spatial location in the imaged volume and each comprising an intensity value corresponding to an intensity of echo signals received from the associated spatial location in the imaged volume;
      receive a tissue parameter map comprising one or more tissue parameter values for each of the plurality of first voxels;
      generate a 3D rendering dataset comprising a plurality of second voxels by assigning one or more material property values to each of the plurality of second voxels, wherein the one or more material property values assigned to each of the plurality of second voxels is based, at least in part, on the intensity value associated with the respective first voxel of the B-mode image, and further based, at least in part, on a tissue parameter value associated with the respective voxel obtained from the tissue parameter map; and
      generate an enhanced B-mode rendering from the 3D rendering dataset, wherein generating the enhanced B-mode rendering comprises;
   propagating light rays from a virtual light source through the plurality of second voxels; and
   propagating rays through the plurality of second voxels, wherein the rays are orthogonal to an observation plane of a virtual observer; and
   a display configured to display the enhanced B-mode rendering.

2. The apparatus of claim 1, wherein the processor is further configured to:
   determine a tissue type for individual ones of the plurality of first voxels based, at least in part, on the tissue parameter values; and
   assign the one or more material property values to each of the plurality of second voxels based on a profile of material property values, wherein the profile is based on the tissue type.

3. The apparatus of claim 2, wherein the tissue type is determined by comparing the tissue parameter values to a table of tissue parameter values.

4. The apparatus of claim 1, wherein the processor is further configured to:
   segment the B-mode image to determine a tissue type for individual ones of the plurality of voxels; and
   assign the one or more material property values to each of the plurality of second voxels based on a profile of material property values, wherein the profile is based on the tissue type.

5. The apparatus of claim 4, wherein the B-mode image is segmented using a trained machine learning model.

6. The apparatus of claim 1, wherein the tissue parameter values comprise at least one of speed of sound values, attenuation values, stiffness values, or density values.

7. A method comprising:
   receiving a B-mode image of an imaged volume, wherein the B-mode image comprises a plurality of first voxels, each associated with a different spatial location in the imaged volume and each comprising an intensity value corresponding to an intensity of echo signals received from the associated spatial location in the imaged volume;
   receiving a tissue parameter map comprising one or more tissue parameter values for each of the plurality of first voxels,
   assigning one or more material property values to each of a plurality of second voxels of a 3D rendering dataset, wherein the one or more material property values assigned to each of the plurality of second voxels is based, at least in part, on the intensity value associated with the respective first voxel of the B-mode image, and further based, at least in part, on a tissue parameter value associated with the respective voxel obtained from the tissue parameter map; and
   generating an enhanced B-mode rendering from the 3D rendering dataset, wherein generating the enhanced B-mode rendering comprises;
   propagating light rays from a virtual light source through the plurality of second voxels; and
   propagating rays through the plurality of second voxels, wherein the rays are orthogonal to an observation plane of a virtual observer.

8. The method of claim 7, further comprising:
   segmenting the B-mode image to determine a tissue type for individual ones of the plurality of first voxels, wherein assigning the one or more material property values to each of the plurality of second voxels is based on a profile of material property values, wherein the profile is based on the tissue type.

9. The method of claim 8, wherein the segmenting is performed by a machine learning model.

10. The method of claim 9, further comprising:
    generating simulated ultrasound images from images acquired from another imaging modality; and
    training the machine learning model to segment the B-mode image with the simulated ultrasound images.

11. The method of claim 8, wherein the segmenting comprises analyzing a texture of the B-mode image.

12. The method of claim 8, wherein the segmenting comprises applying anatomical models to the B-mode image.

13. The method of claim 7, further comprising:
    determining a tissue type for individual ones of the plurality of first voxels based, at least in part, on the tissue parameter values; and
    assigning the values of the one or more material properties to each of the plurality of second voxels based on a profile of material property values, wherein the profile is based on the tissue type.

14. The method of claim 13, wherein determining the tissue type comprises comparing the tissue parameter values to a table of tissue parameter values.

15. A method comprising:
    segmenting a B-mode image to determine a tissue type for individual ones of a plurality of first voxels of the B-mode image;
    assigning one or more material property values to each of a plurality of second voxels of a 3D rendering dataset, wherein the one or more material property values are based, at least in part, on the tissue type;

generating an enhanced B-mode rendering from the 3D rendering dataset, wherein generating the enhanced B-mode rendering comprises:
  propagating light rays from a virtual light source through the plurality of second voxels; and
  propagating rays through the plurality of second voxels, wherein the rays are orthogonal to an observation plane of a virtual observer; and
displaying the enhanced B-mode rendering on a display.

16. The method of claim 15, wherein the segmenting comprises analyzing the B-mode image with at least one of an artificial intelligence or machine learning model.

17. The method of claim 16, wherein the artificial intelligence or the machine learning model comprises a neural network.

18. The method of claim 15, wherein the segmenting comprises analyzing tissue parameter values from a tissue parameter map associated with the plurality of first voxels of the B-mode image.

* * * * *